(12) United States Patent
Saito et al.

(10) Patent No.: US 8,562,132 B2
(45) Date of Patent: Oct. 22, 2013

(54) PHOTOMETRY DEVICE

(75) Inventors: Takashi Saito, Hirakata (JP); Hiroki Noguchi, Sanda (JP); Naohiro Toda, Osaka (JP); Ayako Tsukitani, Kyoto (JP); Kouji Nishioka, Kurayoshi (JP); Akira Takasima, Kobe (JP); Kaoru Ibara, Osaka (JP); Kensuke Yamazoe, Kadoma (JP); Hiroe Kubo, Neyagawa (JP); Yoshinori Karasawa, Minoh (JP)

(73) Assignee: Panasonic Corporation, Osaka (JP)

( * ) Notice: Subject to any disclaimer, the term of this patent is extended or adjusted under 35 U.S.C. 154(b) by 148 days.

(21) Appl. No.: 13/180,632

(22) Filed: Jul. 12, 2011

(65) Prior Publication Data
US 2012/0075583 A1     Mar. 29, 2012

(30) Foreign Application Priority Data
Jul. 12, 2010  (JP) ................................ 2010-158246

(51) Int. Cl.
*A61B 3/00* (2006.01)
*A61B 3/12* (2006.01)

(52) U.S. Cl.
CPC .................. *A61B 3/00* (2013.01); *A61B 3/1208* (2013.01); *A61B 3/1225* (2013.01)
USPC ............................ 351/200; 351/218; 351/221

(58) Field of Classification Search
CPC ....... A61B 3/1208; A61B 3/00; A61B 3/1225
USPC ............ 351/200, 205, 213, 221, 245, 216, 21
See application file for complete search history.

(56) References Cited

U.S. PATENT DOCUMENTS 7,258,438 B2 *   8/2007  Van Derlofske et al. ...... 351/205
2004/0252275 A1  12/2004  Van Derlofske et al.

FOREIGN PATENT DOCUMENTS

| CN | 101430225 | 7/2008 |
| CN | 101799323 | 8/2010 |
| CN | 101799324 | 8/2010 |
| JP | H01233328 | 9/1989 |
| JP | 2-205731  | 8/1990 |

OTHER PUBLICATIONS

The extended European Search Report dated Nov. 16, 2011.
XP002661680, Database WPI Week 200935, Thomson Scientific, London GB AN 2009-J46460.
XP002661681, Database WPI Week 201062, Thomson Scientific, London GB AN 2010-L05254.
XP002661682, Database WPI Week 201062, Thomson Scientific, London GB AN 2010-L05255.

* cited by examiner

*Primary Examiner* — Huy K Mai
(74) *Attorney, Agent, or Firm* — Bacon & Thomas, PLLC

(57) ABSTRACT

In a photometry device, photopic vision luminance Lp is measured by a first luminance measuring unit including a first light filter 4 and a first photoelectric converter 5, and scotopic vision luminance Ls is measured by a second luminance measuring unit including a second light filter 6 and a second photoelectric converter 7. A calculation part 8 calculates mesopic vision luminance Lmes based on a measurement value (photopic vision luminance Lp) of the first luminance measuring unit and a ratio of a measurement value (scotopic vision luminance Ls) of the second luminance measuring unit to the measurement value (photopic vision luminance Lp) of the first luminance measuring unit. Consequently, the photometry device can improve measurement accuracy of the brightness (mesopic vision luminance) in mesopic vision.

5 Claims, 3 Drawing Sheets

FIG.2

| Ls/Lp | Lp 0.01 | 0.03 | 0.1 | 0.3 | 1 | 3 | 4.5 |
|---|---|---|---|---|---|---|---|
| 0.25 | 0.0023 | 0.0145 | 0.0705 | 0.2467 | 0.913 | 2.9265 | 4.4782 |
| 0.35 | 0.0035 | 0.0174 | 0.075 | 0.2545 | 0.9253 | 2.9367 | 4.4812 |
| 0.45 | 0.0045 | 0.0198 | 0.0793 | 0.262 | 0.9373 | 2.9468 | 4.4842 |
| 0.55 | 0.0057 | 0.022 | 0.0834 | 0.2693 | 0.9492 | 2.9568 | 4.4872 |
| 0.65 | 0.0068 | 0.0239 | 0.0873 | 0.2764 | 0.9608 | 2.9666 | 4.4901 |
| 0.75 | 0.0079 | 0.0258 | 0.0911 | 0.2833 | 0.9722 | 2.9763 | 4.4929 |
| 0.85 | 0.0088 | 0.0275 | 0.0947 | 0.2901 | 0.9835 | 2.9859 | 4.4958 |
| 0.95 | 0.0096 | 0.0292 | 0.0983 | 0.2967 | 0.9945 | 2.9953 | 4.4986 |
| 1.05 | 0.0104 | 0.0308 | 0.1017 | 0.3032 | 1.0054 | 3.0046 | 4.5014 |
| 1.15 | 0.0111 | 0.0323 | 0.1051 | 0.3096 | 1.0161 | 3.0139 | 4.5041 |
| 1.25 | 0.0118 | 0.0338 | 0.1083 | 0.3158 | 1.0267 | 3.023 | 4.5068 |
| 1.35 | 0.0125 | 0.0353 | 0.1115 | 0.322 | 1.0371 | 3.0319 | 4.5095 |
| 1.45 | 0.0132 | 0.0367 | 0.1147 | 0.328 | 1.0473 | 3.0408 | 4.5122 |
| 1.55 | 0.0138 | 0.0381 | 0.1178 | 0.3339 | 1.0575 | 3.0496 | 4.5148 |
| 1.65 | 0.0145 | 0.0395 | 0.1208 | 0.3398 | 1.0674 | 3.0582 | 4.5174 |
| 1.75 | 0.0151 | 0.0408 | 0.1238 | 0.3455 | 1.0773 | 3.0668 | 4.52 |
| 1.85 | 0.0157 | 0.0421 | 0.1267 | 0.3512 | 1.087 | 3.0753 | 4.5225 |
| 1.95 | 0.0163 | 0.0434 | 0.1295 | 0.3568 | 1.0966 | 3.0838 | 4.525 |
| 2.05 | 0.0169 | 0.0446 | 0.1324 | 0.3623 | 1.106 | 3.0919 | 4.5275 |
| 2.15 | 0.0174 | 0.0459 | 0.1352 | 0.3677 | 1.1154 | 3.1001 | 4.5299 |
| 2.25 | 0.018 | 0.0471 | 0.1379 | 0.3731 | 1.1246 | 3.1082 | 4.5323 |
| 2.35 | 0.0185 | 0.0483 | 0.1406 | 0.3784 | 1.1338 | 3.1162 | 4.5347 |
| 2.45 | 0.0191 | 0.0495 | 0.1433 | 0.3836 | 1.1428 | 3.1241 | 4.5371 |
| 2.55 | 0.0196 | 0.0506 | 0.1459 | 0.3888 | 1.1517 | 3.1319 | 4.5395 |
| 2.65 | 0.0201 | 0.0518 | 0.1485 | 0.3939 | 1.1605 | 3.1396 | 4.5418 |
| 2.75 | 0.0207 | 0.0529 | 0.1511 | 0.3989 | 1.1693 | 3.1473 | 4.5441 | ated
PHOTOMETRY DEVICE

FIELD OF THE INVENTION

The invention relates to a photometry device for measuring brightness in scotopic and mesopic vision.

BACKGROUND OF THE INVENTION

Spectral luminous efficiency of human eyes varies in photopic, scotopic, and mesopic visions. In photopic vision, cone cells are in function to sense colors. In scotopic vision, although colors are not perceivable because no cone cells are in function, rod cells operate to improve color-sensitivity. In mesopic vision, which is an intermediate state of the photopic vision and the scotopic vision, both the cone and rod cells are in function. Herein, the spectral luminous efficiency in photopic vision has a peak wavelength of about 555 nm. On the other hand, the spectral luminous efficiency in scotopic vision has a shifted peak wavelength of about 507 nm. Such phenomenon is well known as "Purkinje phenomenon."

As an index of the brightness sensed by human eyes, luminance and illuminance are typically employed. As for conventional luminance and illumination meters, however, the luminance and illuminance are measured based on the spectral luminous efficiency in photopic vision. Accordingly, measurement values of the luminance and illumination meters in scotopic and mesopic visions differ from the brightness actually sensed by human eyes.

In a conventional example disclosed in Japanese Patent Application Laid-open No. H2-205731, mesopic-vision equivalent luminance of a light source is calculated from measurement values of luminance and correlated color temperature, based on such knowledge that the correlated color temperature and the luminance of the light source (luminance in photopic vision, i.e., photopic-vision equivalent luminance) correlate with the mesopic-vision equivalent luminance.

However, since a relationship between the spectral luminous efficiency in mesopic vision and the color temperature of the light source is indefinite, such conventional example is not widely spread due to its low validity of the measurement value.

SUMMARY OF THE INVENTION

In view of the above, an object of the present invention is to provide a photometry device capable of improving its measurement accuracy of brightness in mesopic vision.

A photometry device in accordance with one aspect of the invention includes: a first luminance measuring unit for measuring luminance in photopic vision; a second luminance measuring unit for measuring luminance in scotopic vision; and a calculation unit for calculating luminance in mesopic vision from a first measurement value of the first luminance measuring unit and a second measurement value of the second luminance measuring unit, wherein the calculation unit calculates the luminance in mesopic vision based on the first measurement value and a ratio of the second measurement value to the first measurement value.

The photometry device may further include: a spectral unit for dispersing incident light; and a measuring part for measuring light intensity for each of wavelength bands obtained by the spectral unit, wherein the first luminance measuring unit calculates the luminance in photopic vision by integrating the measurement values of the measuring part according to a spectral luminous efficiency in photopic vision; and the second luminance measuring unit calculates the luminance in scotopic vision by integrating the measurement values of the measuring part according to a spectral luminous efficiency in scotopic vision.

The photometry device of the invention can improve measurement accuracy of brightness in mesopic vision.

BRIEF DESCRIPTION OF THE DRAWINGS

The objects and features of the present invention will become apparent from the following description of embodiments, given in conjunction with the accompanying drawings, in which:

FIG. 2 is an explanatory view of a data table; and

DETAILED DESCRIPTION OF THE EMBODIMENT

First Embodiment

Figure 1:
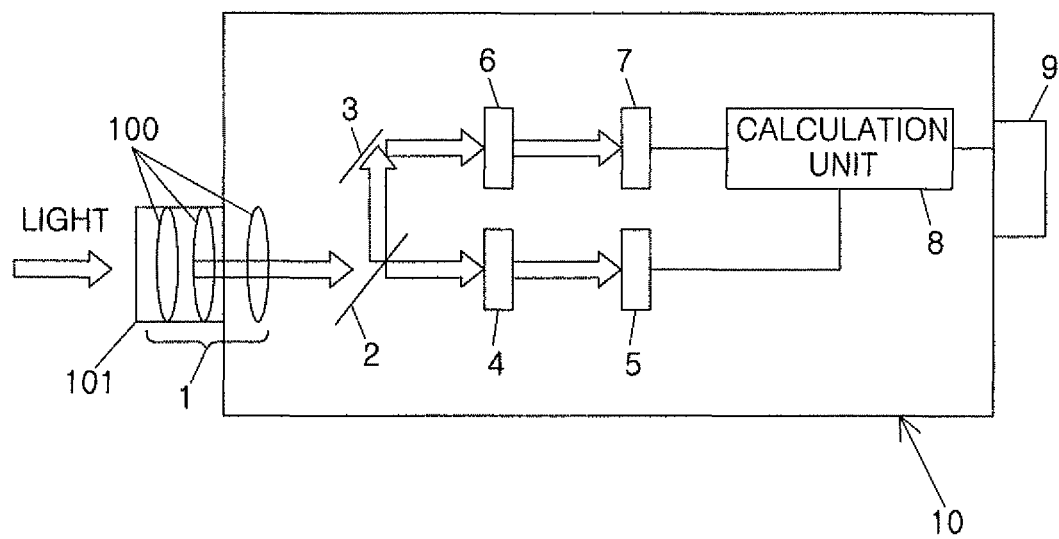
FIG. 1 is a block diagram showing a first embodiment of a photometry device in accordance with the present invention.

A photometry device of the present embodiment is, as shown in FIG. 1, provided with an optical part 1, a half mirror 2, a mirror 3, a first light filter 4, a first photoelectric converter 5, a second light filter 6, a second photoelectric converter 7, a calculation part 8, a display 9, and a housing 10.

The housing 10 has a box-like shape and is made of a synthetic resin or a metal. Light is introduced in the housing 10 through a hole opened in the left side thereof.

The optical part 1 includes a plurality of convex lenses 100; and a cylindrical body 101 supporting the convex lenses 100 and closing the hole of the housing 10. Accordingly, the light introduced through the hole is converged by the convex lens 100 of the optical part 1.

The half mirror 2 is disposed on an optical path of the optical part 1, and splits the light converged by the optical part 1 into two parts. On one optical path branched by the half mirror 2, the first light filter 4 is disposed. The first light filter 4 has filter characteristics corresponding to human spectral luminous efficiency in photopic vision (hereinafter, referred to as "photopic vision spectral luminous efficiency"), and is formed of, for example, dielectric multilayers.

The other optical path branched by the half mirror 2 is bent at an angle of 90 degrees by the mirror 3. On the optical path bent by the mirror 3, the second light filter 6 is disposed. The second light filter 4 has filter characteristics corresponding to human spectral luminous efficiency in scotopic vision (hereinafter, referred to as "scotopic vision spectral luminous efficiency"), and is formed of, for example, dielectric multilayers.

The first photoelectric converter 5 mainly includes: a photoelectric transducer (not shown) that converts the light passing through the first light filter 4 into electric signals; and an amplifier (not shown) that amplifies an output voltage of the photoelectric transducer. Thus, the output voltage of the first photoelectric converter 5 represents the luminance (photopic vision luminance) Lp in photopic vision.

Similar to the first photoelectric converter 5, the second photoelectric converter 7 mainly includes: a photoelectric transducer (not shown) that converts the light passing through the second light filter 6 into electric signals; and an amplifier (not shown) that amplifies an output voltage of the photoelectric transducer. Thus, the output voltage of the second photoelectric converter 7 represents the luminance (scotopic vision luminance) Ls in scotopic vision.

The calculation part 8 primarily includes: an A-D converter (not shown) for quantizing (A-D converting) each of the output voltages of the first photoelectric converter 5 and the second photoelectric converter 7; a memory (not shown) in which a program for performing calculation described later is stored; and a CPU (not shown) for executing the program stored in the memory. By executing the program in the CPU, the calculation part 8 calculates the luminance Lmes in mesopic vision (mesopic vision luminance) as follows. Specifically, the calculation part 8 calculates a ratio of the scotopic vision luminance Ls to the photopic vision luminance Lp (=Ls/Lp) and then obtains the mesopic vision luminance Lmes, with reference to the data table shown in FIG. 2, from the photopic vision luminance Lp and the ratio. For instance, when photopic vision luminance Lp=0.1 and ratio (Ls/Lp)=0.85 are given, the mesopic vision luminance Lmes=0.0947 is obtained from the data table in FIG. 2.

The display 9 includes a display device (not shown) such as a liquid crystal display, and a driver circuit (not shown) for driving the display device. The driver circuit drives the display device according to display signals outputted from the calculation part 8 to display the value of the mesopic vision luminance Lmes (Lmes=0.0947 in the above example) on the display device.

Note that the data table shown in FIG. 2, which is obtained by previous experiments, is stored in the memory of the calculation part 8. The data table is, however, exemplary and not limited to this. In the case where the value of the photopic vision luminance Lp or the ratio does not exist in the data table, the calculation part 8 calculates the mesopic vision luminance Lmes from the nearest values by interpolation. Alternatively, instead of utilizing the data table, the mesopic vision luminance Lmes may be calculated by using pre-determined calculation expressions.

As described above, in the photometry device of the present embodiment, the first luminance measuring unit, including the first light filter 4 and the first photoelectric converter 5, measures the photopic vision luminance Lp, and the second luminance measuring unit, including the second light filter 6 and the second photoelectric converter 7, measures the scotopic vision luminance Ls. Then, the calculation part 8 calculates the mesopic vision luminance Lmes based on the measurement value (photopic vision luminance Lp) of the first luminance measuring unit and the ratio of the measurement value of the second luminance measuring unit (scotopic vision luminance Ls) to the measurement value of the first luminance measuring unit (photopic vision luminance Lp). Consequently, the photometry device of the present embodiment can improve measurement accuracy of brightness in mesopic vision (mesopic vision luminance).

Second Embodiment

Figure 3:
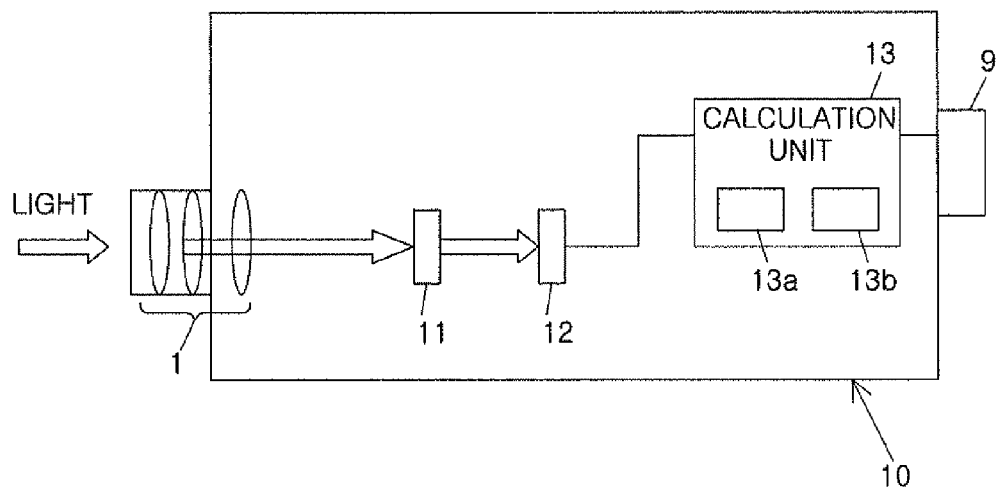
FIG. 3 is a block diagram showing a second embodiment of the photometry device in accordance with the present invention.

A photometry device of the present embodiment, as shown in FIG. 3, includes: a spectral filter 11 for dispersing incident light; a measuring part 12 for measuring intensities (luminance) of the lights dispersed into a plurality of wavelength bands at each wavelength band; and a calculation part 13 for calculating mesopic vision luminance. The same reference numerals are assigned to the common components to the photometry device of the first embodiment, and the description thereof will be omitted.

The spectrum filter 11 is configured of a prism, and divides (disperses) incident light into a plurality of wavelength bands by utilizing its different refractive indexes depending on the wavelengths of the light. The measuring part 12 has a plurality of photoelectric transducers (not shown) corresponding to each of the wavelength bands of the light dispersed by the spectrum filter 11, and a plurality of amplifiers (not shown) amplifying output voltages of the respective photoelectric transducers.

The calculation part 13 mainly includes: an A-D converter (not shown) for quantizing (A-D converting) the output voltages of the measuring part 12; a memory (not shown) in which a program for executing a calculation described later is stored; and a CPU (not shown) for executing the program stored in the memory. By executing the program in the CPU, the calculation part 13 calculates the photopic vision luminance Lp, the scotopic vision luminance Ls, and the mesopic vision luminance Lmes as follows.

The calculation part 13 is provided with a photopic vision luminance calculating part 13a calculating the photopic vision luminance Lp in such a way that the measurement value at each of the wavelength bands measured by the measuring part 12 is weighted corresponding to photopic vision luminous efficiency. For instance, provided that a wavelength band including peak wavelength (555 nm) has a weighting factor of 1, the photopic vision luminance calculating part 13a calculates the photopic vision luminance Lp in such a way that the measurement values are integrated after being multiplied by weighting factors less than 1 that become smaller as they go away from the wavelength band.

Likewise, the calculation part 13 has a scotopic vision luminance calculating part 13b calculating the scotopic vision luminance Ls in such a way that the measurement value at each of the wavelength bands measured by the measuring part 12 is weighted corresponding to scotopic vision luminous efficiency. For instance, provided that a wavelength band including peak wavelength (507 nm) has a weighting factor of 1, the scotopic vision luminance calculating part 13b calculates the scotopic vision luminance Ls in such a way that the measurement values are integrated after being multiplied by weighting factors less than 1 that become smaller as they go away from the wavelength band. Namely, in the photometry device of the present embodiment, the photopic vision luminance calculating part 13a and the scotopic vision luminance calculating part 13b of the calculation part 13 serve as the first luminance measuring unit and the second luminance measuring unit, respectively.

Furthermore, the calculation part 13, as in the first embodiment, calculates the ratio (=Ls/Lp) of the scotopic vision luminance Ls to the photopic vision luminance Lp, and then obtains the luminance Lmes, with reference to the data table shown in FIG. 2, from the photopic vision luminance Lp and the ratio.

As described above, the photometry device of the present embodiment also can improve measurement accuracy of brightness (mesopic vision luminance) in mesopic vision as well as the first embodiment. Further, the photometry device of the present embodiment uses only the spectrum filter 11, whereas two filters, the first light filter 4 and the second light filter 6, are used in the first embodiment. Therefore, the photometry device of the present embodiment has such an advantage that a measurement error depending on the filter accuracy becomes smaller than that of the first embodiment. Moreover, in the photometry device of the present embodiment, light intensity (luminance) for each of the wavelength bands is measured, thereby enabling the calculation part 13 to calculate other indices, such as a color rendering index.

While the invention has been shown and described with respect to the embodiments, it will be understood by those skilled in the art that various changes and modification may be made without departing from the scope of the invention as defined in the following claims.

What is claimed is:

1. A photometry device comprising:
a first luminance measuring unit configured to measure luminance in photopic vision;
a second luminance measuring unit configured to measure luminance in scotopic vision; and
a calculation part configured to obtain luminance in mesopic vision from a data table based on a first measurement value of the first luminance measuring unit and a ratio of a second measurement value of the second luminance measuring unit to the first measurement value.

2. The photometry device as set forth in claim 1, further comprising:
a spectral unit configured to disperse incident light; and
a measuring part configured to measure light intensity for each of wavelength bands obtained by the spectral unit,
wherein the first luminance measuring unit integrates measurement values of the measuring part according to a spectral luminous efficiency in photopic vision to measure the luminance in photopic vision; and
the second luminance measuring unit integrates measurement values of the measuring part according to a spectral luminous efficiency in scotopic vision to measure the luminance in scotopic vision.

3. The photometry device as set forth in claim 1, wherein the first luminance measuring unit comprises: a first light filter having filter characteristics corresponding to a spectral luminous efficiency in photopic vision; and a first photoelectric converter configured to convert light passing through the first light filter into electric signals, and
wherein the second luminance measuring unit comprises: a second light filter having filter characteristics corresponding to a spectral luminous efficiency in scotopic vision; and a second photoelectric converter configured to convert light passing through the first light filter into electric signals.

4. The photometry device as set forth in claim 3, further comprising:
an optical part configured to convert light; and
a half mirror configured to split the light converged by the optical part into two parts,
wherein the first light filter is disposed on one optical path branched by the half mirror and the second light filter is disposed on the other optical path branched by the half mirror.

5. The photometry device as set forth in claim 1, when at least one of the first measurement value and the ratio of the second measurement value to the first measurement value does not exist in the data table, the calculation part calculates the luminance in mesopic vision by interpolation of luminances in mesopic vision in the data table.

* * * * *